United States Patent
Koch et al.

(10) Patent No.: US 6,167,747 B1
(45) Date of Patent: Jan. 2, 2001

(54) APPARATUS FOR DETECTING HYDROCARBON USING CRYSTAL OSCILLATORS WITHIN FUEL DISPENSERS

(75) Inventors: Wolfgang H. Koch, Batavia; Arthur R. Brown, Warrenville, both of IL (US)

(73) Assignee: Tokheim Corporation, Fort Wayne, IN (US)

(*) Notice: Under 35 U.S.C. 154(b), the term of this patent shall be extended for 0 days.

(21) Appl. No.: 09/134,116

(22) Filed: Aug. 14, 1998

(51) Int. Cl.[7] .............................. B67D 5/378; B65B 1/04; G01N 29/02
(52) U.S. Cl. ...................... 73/19.03; 73/23.31; 73/24.01; 141/59; 141/83; 141/94
(58) Field of Search ............................ 73/19.03, 23.31, 73/24.01; 141/59, 94, 392, 83

(56) References Cited

U.S. PATENT DOCUMENTS

| | | |
|---|---|---|
| 3,164,004 | 1/1965 | King, Jr. ............................... 73/24.06 |
| 3,478,573 | 11/1969 | King, Jr. . |
| 3,828,607 | 8/1974 | Janzen et al. ........................ 73/24.06 |
| 3,879,992 | 4/1975 | Bartera . |
| 3,932,807 | 1/1976 | Wilson . |
| 4,446,720 | 5/1984 | Sinclair . |
| 4,561,286 | 12/1985 | Sekler et al. . |
| 4,674,319 | 6/1987 | Muller et al. . |
| 4,730,478 | 3/1988 | Gedeon . |
| 4,735,081 | 4/1988 | Luoma et al. . |
| 4,782,334 | 11/1988 | Meaney . |
| 4,785,658 | 11/1988 | Jackson . |
| 5,400,643 | 3/1995 | De Angelis et al. . |
| 5,477,716 | 12/1995 | Snow . |
| 5,507,325 | * 4/1996 | Finlayson .............................. 73/23.2 |
| 5,782,275 | * 7/1998 | Hartsell, Jr. et al. .................. 141/94 |

* cited by examiner

Primary Examiner—Daniel S. Larkin
(74) Attorney, Agent, or Firm—Randall J. Knuth

(57) ABSTRACT

A vapor recovery system is disclosed that utilizes a crystal oscillator for sensing the presence of hydrocarbon in the vapor emissions emanating from a fuel tank during refueling. The crystal oscillator is coated with a layer of material having a sensitivity for hydrocarbon. In response to any interaction between the coating layer and hydrocarbon, the crystal oscillator experiences a shift in its oscillation frequency relative to the fundamental resonance frequency. The frequency shift is representative of the hydrocarbon concentration in the vapor emissions. A control signal based on the frequency shift is generated and then used to adjust the operating speed of the vapor pump.

18 Claims, 2 Drawing Sheets

APPARATUS FOR DETECTING HYDROCARBON USING CRYSTAL OSCILLATORS WITHIN FUEL DISPENSERS

BACKGROUND OF THE INVENTION

1. Field of the Invention

The present invention relates to vapor recovery systems used in connection with fuel dispensing apparatus, and, more particularly, to a method and system for monitoring the vapor emissions and adjusting the flow rate of pumped vapors in response to low levels of detected hydrocarbon.

2. Description of the Related Art

The fuel tanks of serviced vehicles contain both a liquid component corresponding to the fuel dispensed into the tank and a vapor component overlying the fuel level and corresponding to a volume of volatilized fuel vapors. Refueling the vehicle will result in fuel vapors being discharged into the atmosphere since any gasoline flowing into the fuel tank will displace an equivalent volume of the volatilized vapors and thereby force such displaced vapors out of the tank. Increased awareness of the adverse impact of vapor pollutants on the environment has prompted governmental authorities to require that fuel dispensing systems be designed to eliminate the release of vapors into the atmosphere, preferably by collecting the vapors for storage and possible recycling. The response of industry has been to develop various systems designed to collect and return the fugitive vapor emissions to a storage tank, such as the underground facility located on-site at the service station where the fuel supply is maintained. The recovered vapors may be further transported to a processing site where the vapors are returned to liquid form in a recycling operation.

One class of conventional vapor recovery systems utilizes a vacuum pump to assist in the collection of fuel vapors and their subsequent transfer to the storage tank. The vacuum pump draws fugitive vapors into an intake line and conveys the collected vapors back to the storage tank. The aspirating action generated by the vacuum pump is normally sufficient to capture the vapor emissions, thereby obviating the need for any sealing structure such as a bellows element, and only requiring that the inlet port of the vapor intake line be disposed in close proximity to the filler neck of the fuel tank from where the vapors emanate.

In all such vacuum-assist vapor recovery systems, it is critically important that the volume of vapor emissions being collected closely approximate the volume of vapor being displaced by the gasoline flowing into the fuel tank. Otherwise, if the volume of vapor being collected is less than that being displaced, the non-recovered portion will be discharged into the atmosphere. Conversely, if the volume of vapor being collected is greater than the volume being emitted from the tank, the excess volume will consist of atmospheric components that are recovered along with the vapors.

Several configurations have been proposed that focus upon making calculated adjustments to the flow rate generated by the vapor pump based upon measurements produced by sensing apparatus that monitor the fueling and vapor recovery operations. In one such representative configuration disclosed in U.S. Pat. No. 5,355,915 to Payne, there is provided a vapor recovery system including a vapor pump driven by an electric motor, and further including sensors to generate pulse train signals representative of the flow rate of both the liquid fuel pump and the vapor pump. A controller is provided to control the speed of the vapor pump based upon a comparison of the flow rates of the liquid fuel pump and vapor pump, as indicated by their respective pulse train signals. In particular, the operating speed of the vapor pump is adjusted so that the vapor pump flow rate is equalized with the liquid fuel flow rate. The overall purpose of tracking the vapor flow rate to the liquid fuel rate is to ensure that the volumetric quantity of retrieved vapor is the same as the volumetric quantity of vapor being displaced by the dispensed fuel. However, since adjustments to the vapor flow rate are made on the basis of measurements (i.e., volumetric flow rates) that are not specifically representative of the hydrocarbon concentration of the recovered vapors, the flow rate equalization process may not in fact be sufficiently accurate or reliable in its attempt to precisely regulate the composition of the recovered vapors.

In another prior art vapor recovery configuration disclosed in U.S. Pat. No. 5,507,325 to Finlayson, an array of sensors are provided to produce signals representative of the vapor-to-air ratio as measured at a variety of positions located proximate to the tank opening. A controller is provided to determine a baseline collection rate for the vapor pump based on the liquid fuel flow rate; the initial pump rate is then adjusted according to the signals generated by the vapor-to-air ratio sensors in order to minimize the amount of fuel vapors that escape into the atmosphere, and to minimize the amount of air contained in the gaseous mixture that is drawn along the vapor intake line.

The vapor recovery system of Finlayson is an advance over the systems described above because it provides a means by which the compositional content of the recovered emissions (i.e., vapor versus air) can be directly measured. This permits a more accurate evaluation of whether the vapor pump is inducing the proper volumetric flow of fugitive emissions into the recovery line. However, one significant problem attending the Finlayson system stems from the fact that the sensors are susceptible to a permanent condition of producing false readings in the event that vapor condensate settles onto the sensor surfaces. Vapor condensation within the intake line is a recurring problem that results when differentials in temperature and pressure throughout the vapor recovery system reach threshold conditions. The accumulation or even transient deposition of condensed fuel vapors on fuel-detecting sensors will produce false measurements of the fuel content in the monitored environment and lead to improper adjustment of the vapor pump rate.

What is therefore needed in the art is a system that monitors the fugitive vapor emissions displaced from a tank during refueling and that adjusts the vapor recovery rate based on direct measurements of the hydrocarbon concentration in the monitored environment. Such a system must also be capable of accommodating both vapor and liquid forms of the emissions in its measurement apparatus, and be able to remove condensate from its sensor elements to avoid false readings of the hydrocarbon content.

SUMMARY OF THE INVENTION

The present invention provides a vapor recovery system that monitors the vapor emissions emanating from a fuel tank during refueling and generates detection data indicating the hydrocarbon concentration in the vapor stream. This measurement of the hydrocarbon content is then used as the basis for appropriately adjusting the operating speed of the vapor pump. The sensing apparatus includes a crystal oscillator coated with a layer of material capable of interacting with hydrocarbon and which induces a shift in the oscillation frequency of the crystal in response to such interactions.

The invention comprises, in one form thereof, a system for recovering vapor emissions from a fuel receiving tank, comprising a vapor collection means, crystal oscillator means, and controller means. The vapor collection means, which is disposed in vapor communicating relationship with respect to the fuel receiving tank, controllably collects vapor emissions emanating from the fuel receiving tank. The crystal oscillator means, which is exposed for contact with vapor emissions from the fuel receiving tank and is adapted to exhibit a shift from its fundamental resonance frequency in response to the presence of hydrocarbon, generates a frequency shift signal having a frequency of oscillation representative of a hydrocarbon concentration within vapor emissions exposed to the oscillator means. The controller means, which is operatively coupled to the vapor collection means and to the oscillator means, controllably adjusts the rate of vapor collection by the vapor collection means in accordance with the frequency shift signal.

The crystal oscillator means further comprises a resonant crystal structure including at least one surface thereof coated with a material having an affinity for hydrocarbon accretion.

The system further comprises a reference crystal oscillator means for generating a reference frequency signal at the fundamental resonance frequency; mixing means, responsive to the frequency shift signal from the crystal oscillator means and the reference frequency signal from the reference crystal oscillator means, for generating a beat signal indicative of the frequency differential therebetween; and conversion means, operatively coupled to the mixing means, for providing a control signal in accordance with the frequency differential.

The vapor collection means comprises vapor pump means for controllably generating a variable vacuum action that is effective in drawing vapor emissions away from the fuel receiving tank.

The invention comprises, in another form thereof, a system for fueling a receiving tank, comprising fuel dispensing means for dispensing fuel into an inlet of said receiving tank; vapor capturing means, disposed in vapor communicating relationship with respect to the inlet of the receiving tank, for controllably acquiring vapor emissions emanating from the receiving tank; sensor means disposed in vapor sensing relationship with respect to the inlet of the receiving tank for sensing vapor emissions emanating therefrom; and controller means.

The sensor means is adapted for operation in the absence of vapor emissions for generating an oscillatory signal at a fundamental frequency, and is adapted for operation in the presence of vapor emissions for generating an oscillatory signal at a frequency that is shifted relative to the fundamental frequency in accordance with a hydrocarbon concentration within the sensed vapor emissions. The controller means, which is operatively coupled to the vapor capturing means and to the sensor means, controls the acquisition of vapor emissions by the vapor capturing means as a function of the frequency shift.

The sensor means further comprises crystal oscillation circuit means, adapted for interaction with hydrocarbon, for generating a resonant frequency output signal having an oscillation frequency influenced by and indicative of the concentration of hydrocarbon in the vapor emissions sensed by the sensor means. The oscillation frequency of the generated output signal exhibits a frequency shift relative to a fundamental resonant frequency. The oscillation circuit means further includes a resonant crystal structure having a coating layer formed thereon and capable of interacting with hydrocarbon.

The invention comprises, in another form thereof, a system for detecting vapor emissions including hydrocarbon emanating from a fuel receiving tank, comprising vapor collection means for controllably collecting vapor emissions emanating from the fuel receiving tank; vapor monitoring means; and controller means.

The vapor monitoring means, which is disposed for exposure to the vapor emissions and includes an oscillation means comprising a resonant structure having a contact layer formed thereon and which is capable of interacting with hydrocarbon, senses the vapor emissions and provides an oscillatory signal generated by the resonant structure and which is characterized by a frequency of oscillation defining a shift from a fundamental resonance frequency indicating the hydrocarbon concentration in the sensed vapor emissions.

The controller means, which is operatively coupled to the vapor collection means and is responsive to the oscillatory signal provided by the vapor monitoring means, variably controls the collection of vapor emissions by the vapor collection means in accordance with the frequency shift defined by the oscillation frequency of the oscillatory signal.

The invention comprises, in yet another form thereof, a method of recovering vapors from a fuel storage tank, comprising the steps of collecting the vapors with a controllable pumping action generating an adjustable vapor flow rate; providing a resonant crystal structure having a contact structure capable of interacting with hydrocarbon upon exposure thereto and operative to generate a resonance signal having a frequency of oscillation determined by the level of hydrocarbon interaction in the contact structure; exposing the resonant structure for contact with vapor emissions emanating from the fuel storage tank; and controlling the pumping action to adjust the vapor flow rate in accordance with the frequency of oscillation of the resonance signal.

The step of controlling the pumping action further includes the steps of determining a frequency differential between the oscillation frequency of the resonance signal and a fundamental resonance frequency of the resonant crystal structure; converting the determined frequency differential to a control signal representative of hydrocarbon concentration in the vapor emissions; and adjusting the vapor flow rate in accordance with the control signal.

One advantage of the present invention is that the coated crystal oscillator is capable of sensing hydrocarbon in both its gaseous and liquid forms.

Another advantage of the present invention is that the disclosed system reduces interactions between assisted vapor recovery systems and vehicle on-board fueling recovery (ORVR) systems.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
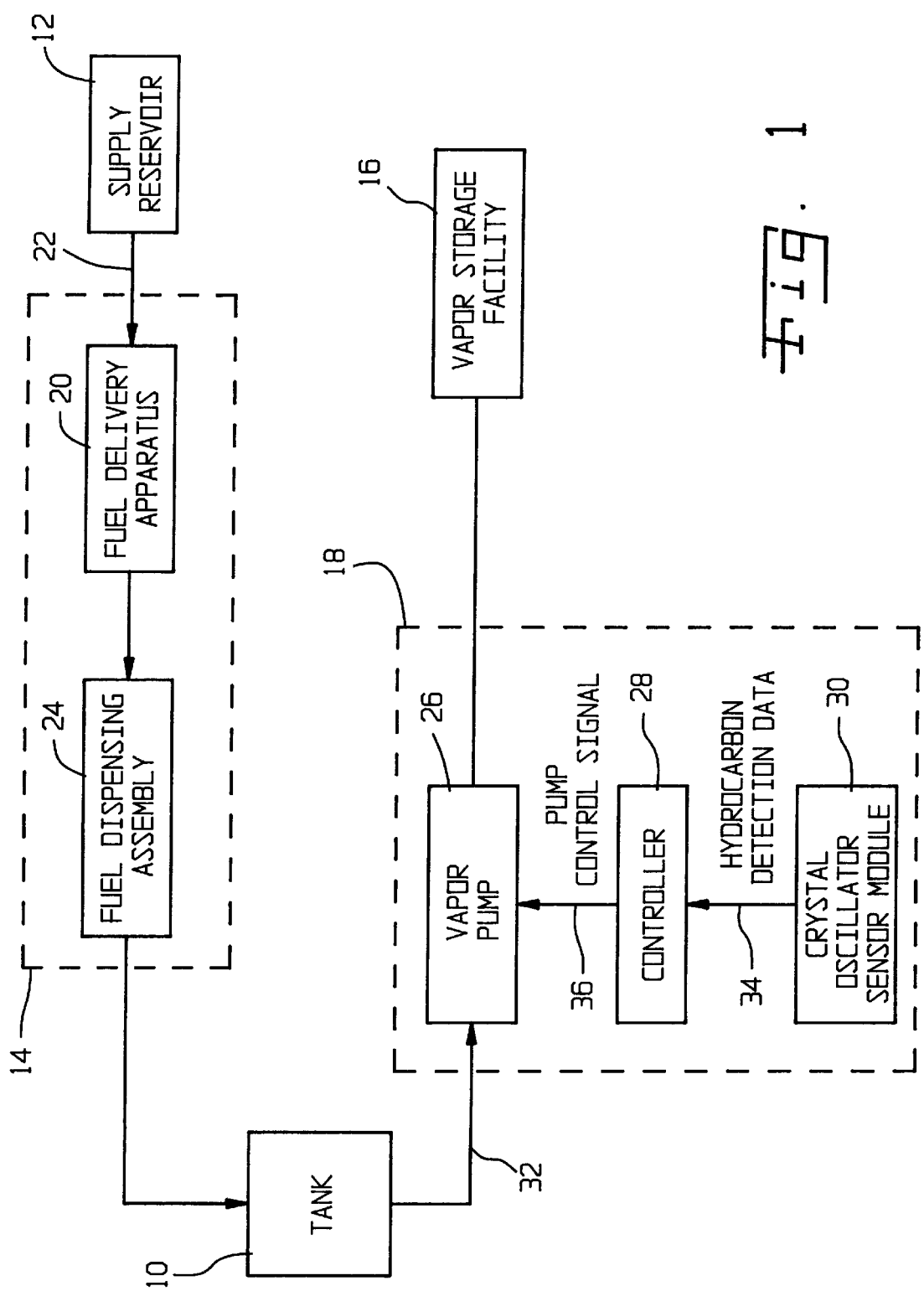
FIG. 1 is a block diagram illustration of a vapor recovery system according to one embodiment of the present invention.

FIG. 1 illustrates in block diagram form a system according to one embodiment of the present invention for fueling a tank 10 with liquid fuel from supply reservoir 12 using fuel delivery system 14, and for collecting and transferring fugitive vapor emissions from tank 10 to vapor storage facility 16 using a vapor recovery system 18. As will be discussed hereinafter in greater detail, the vapor recovery system 18 employs a sensor device implemented with a crystal-based oscillator that is coated with an appropriate film material selected for its ability to interact with hydrocarbon in both its vapor and liquid (i.e., condensate) forms. In response to such interaction, which increases the effective mass of the coating layer, there is induced in the crystal a shift in the oscillation frequency from its fundamental resonant frequency. The frequency shift indicates the amount of hydrocarbon interacting with the coating and hence provides a measure of the concentration of hydrocarbon in the vapor stream. The detected hydrocarbon concentration is used as the basis for determining what adjustments, if necessary, to make to the operating speed of the vapor pump, which forms a part of vapor recovery system 18.

The illustrated system is particularly useful in fueling activity oriented towards unsupervised consumer operation. Accordingly, in these applications, tank 10 corresponds to the fuel tank of a vehicle and the supply reservoir 12 corresponds to the fuel storage chamber typically located in an underground facility on the premises of a service station. It is conventional in the industry for the recovered vapors to be routed back to supply reservoir 12, obviating the need for any separately constructed vapor storage facility 16.

The fuel delivery system 14 includes a fuel delivery apparatus 20 coupled to supply reservoir 12 and operative to pump liquid fuel from supply reservoir 12 along fuel line 22. System 14 further includes a fuel dispensing assembly 24 coupled to fuel delivery apparatus 20 and adapted to be engageable with an opening of tank 10 for dispensing the pumped liquid fuel into tank 10. In automotive applications, the fuel dispensing assembly 24 will preferably be configured in the form of a nozzle member having a dispensing portion that is insertable, at least in part, into a filler neck defining the refueling inlet passageway of tank 10. The fuel delivery system 14 is well known to those skilled in the art and is generally representative of any arrangement capable of delivering fuel to tank 10.

The interior of tank 10 will generally consist of a quantity of liquid fuel, with the remaining volume being occupied by volatilized fuel vapors. The process of dispensing liquid fuel into tank 10 causes a certain volume of the volatilized fuel vapors to be thereby displaced and forced out of tank 10 through its refueling orifice. The vapor recovery system 18 of the present invention is designed to capture these displaced fugitive vapor emissions while minimizing the collection of atmospheric air.

The illustrated vapor recovery system 18 includes a vapor pump 26, a controller 28, and a crystal oscillator sensor module 30 that operates to detect the presence of hydrocarbon within vapor emissions and to provide a measurement representing the concentration of any detected hydrocarbon. In brief, system 18 operates so that vapor emissions displaced from tank 10 are collected under the influence of a vacuum action generated by vapor pump 26, which produces a volumetric vapor flow whose rate is regulated by controller 28 in accordance with the hydrocarbon concentration detected by sensor module 30.

Vapor pump 26 is preferably coupled to a vapor passageway represented by vapor intake line 32, which is disposed in a sufficiently proximate relationship relative to the opening of tank 10 so that substantially all of the displaced vapors can be recovered through vapor intake line 32. The vapor passageway may be formed as an annular conduit concentrically disposed around the liquid fuel line that transports fuel to tank 10, and preferably extends from supply reservoir 12 to a termination point at or near the nozzle aperture where the fuel emerges. It should be apparent to those skilled in the art that any type of vapor intake arrangement may be adapted for use in conjunction with the present invention, including, for example, a vapor pipe traversing the interior of the fueling hose.

The vapor pump 26 creates a vacuum or aspirating action that induces vapor emissions proximate the inlet port of vapor intake line 32 to be drawn into line 32 and transported to vapor storage facility 16. The aspirating action induced by vapor pump 26 generates a volumetric flow within vapor intake line 32 that is regulated by the operating speed of vapor pump 26. This operating speed is adjustably controlled by a control signal generated by controller 28. Accordingly, vapor pump 26 produces a volumetric vapor stream within vapor intake line 32 that is characterized by a controllably variable flow rate.

The crystal oscillator sensor module 30 serves a vital function in the vapor collection process of vapor recovery system 18 by providing a measurement of the hydrocarbon concentration in the vapor emissions emanating from the tank during refueling. In accordance with the present invention, sensor module 30 is comprised of an oscillation circuit including a piezoelectric quartz crystal. The crystal forms a resonant structure characterized by a fundamental resonance frequency. It is known that any type of film deposition on any of the major surfaces of the crystal induces a change in the frequency of oscillation of the crystal from its fundamental resonance frequency. Detection of this frequency shift provides a basis for then determining the actual amount of film deposition that occurred during the measurement interval corresponding to the observed frequency shift. This phenomenon is described by J. T. Lue in "Voltage readout of a temperature-controlled thin film thickness monitor", Journal of Physics E: Scientific Instruments, vol. 10, pp. 161–163 (1977), incorporated herein by reference.

Figure 2:
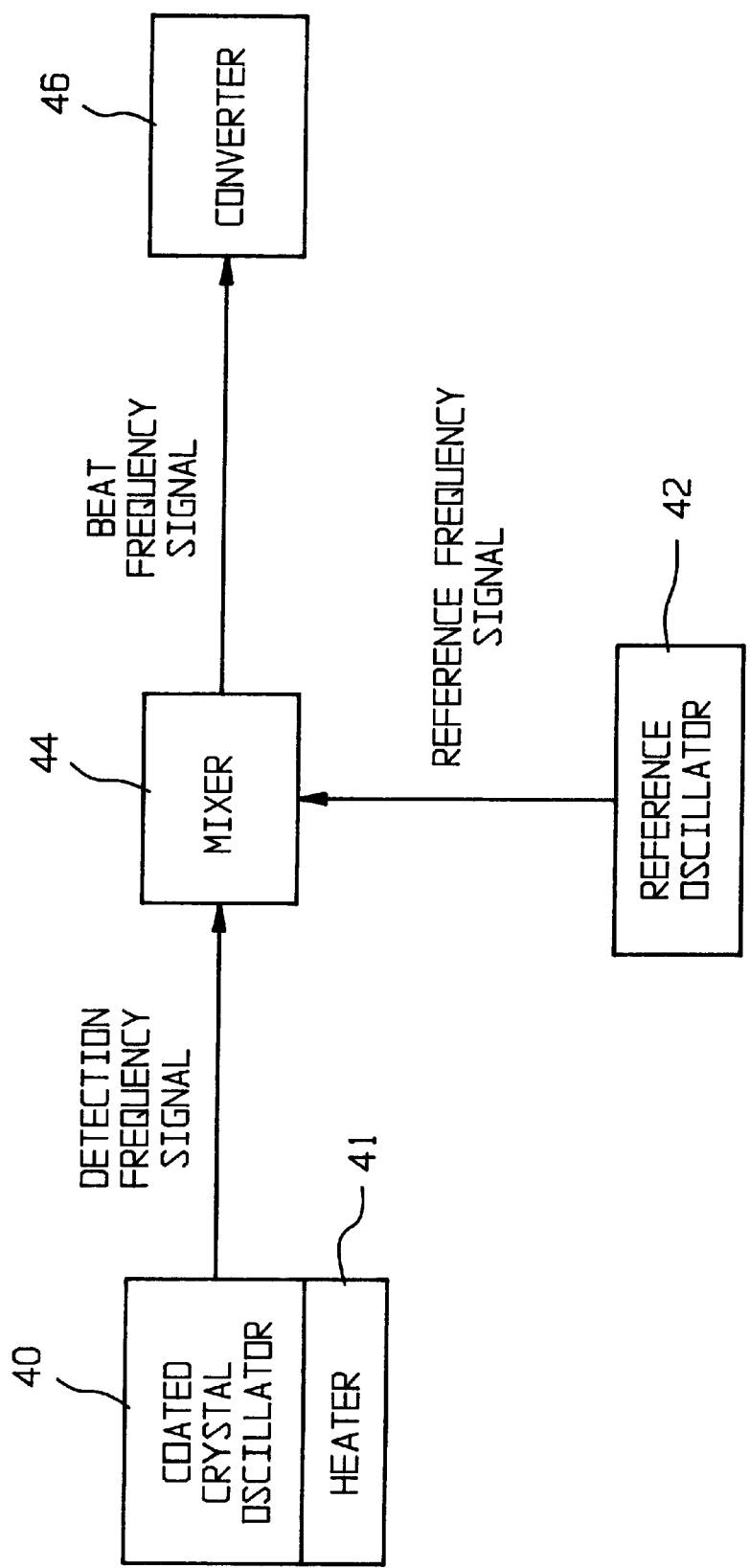
FIG. 2 is a block diagram illustration of the crystal oscillator sensor module disclosed in FIG. 1, according to a preferred embodiment of the present invention.

In accordance with one aspect of the present invention, a film of hydrocarbon-sensitive material is suitably deposited on the crystal to define a contact structure that is exposed for contact with the vapor emissions discharged from the fuel tank. The resulting coated crystal oscillator is characterized in operation by a respective fundamental resonant frequency. The criteria for choosing the deposition material involves selecting a substance having a certain affinity for hydrocarbon and which is capable of sustaining a sufficient interaction with hydrocarbon, thereby allowing the hydrocarbon to become physically associated with the coating material in a type of mass accretion process. The entire fabrication process is preferably oriented towards ensuring that any interaction between the coating material and hydrocarbon is reversible so that the coating structure remains substantially intact and can be restored to its original form. For example, the interaction may involve such phenomenon as reversible absorption and adsorption. A preferred feature of the coating material is its ability to interact with hydrocarbon in liquid form. Variations in pressure and temperature levels within the vapor recovery system typically create conditions favorable to the condensation of vapor emissions. The crystal coating material is selected to be able to accommodate interactions with both gaseous and condensate forms of hydrocarbon. In one preferred configuration of the present invention, the coated crystal oscillator is integrated with a thermal generation unit or heater unit 41, as shown in FIG. 2, that is operative to apply thermal energy to the crystal oscillator as a means of evaporating any condensate being retained by the coating layer. Such heater unit 41 may be controlled by controller 28.

The consequence of this interaction between the coating layer and any hydrocarbon in the vapor emissions is to cause the crystal to experience a shift in its frequency of oscillation from the fundamental resonance frequency to a detection frequency whose oscillatory characteristics are defined by the new crystal oscillator formation having its coating layer altered by the interaction. The frequency shift is therefore representative of the amount of hydrocarbon interacting with the coating layer of the crystal oscillator and hence provides a measure of the hydrocarbon concentration in the emission monitoring environment. The interaction preferably achieves a level of structural equilibrium that is sufficiently stable to allow an accurate measurement of the frequency shift. The crystal oscillator sensor module 30 is provided with means for determining the frequency shift based on the detection frequency generated by the coated crystal oscillator and a reference signal indicating the fundamental resonance frequency. This calculated frequency shift is provided to controller 28 as hydrocarbon detection data 34. As will be described below in further detail, controller 28 generates a pump control signal 36 as a function of the frequency shift embodied in hydrocarbon detection data 34 and applies pump control signal 36 to vapor pump 26, which is effective in regulating the vapor pump operating speed and hence the volumetric flow rate of the vacuum action.

The crystal oscillator component may itself be disposed at any of various detection sites depending upon where it is desired to monitor for the vapor emissions. For example, in order to obtain a measure of the hydrocarbon concentration within the tank, the crystal oscillator may be mounted on any portion of the nozzle that becomes disposed within the interior of tank 10 when the nozzle engages the tank opening to dispense fuel. More preferably, the crystal oscillator may be positioned within vapor intake line 32 in order to detect the hydrocarbon concentration of the recovered vapors. An array of individual crystal oscillators located at various detection sites is capable of generating a position-based hydrocarbon concentration profile that can be used by controller 28 to provide highly precise regulation of vapor pump 26.

Controller 28 is provided with a processor unit that determines the appropriate flow rate that should be generated by vapor pump 26, using the hydrocarbon concentration represented by the hydrocarbon detection data 34 as the basis for determining the flow rate. The vapor flow rate should generally exhibit a direct relationship to the hydrocarbon concentration level. For example, at low concentration levels of hydrocarbon, a reduced flow rate is indicated in order to eliminate or at least minimize the recovery of excess oxygen. It may even be desirable to fully disable vapor pump 26 (i.e., suspend its pumping action) if the hydrocarbon concentration level falls below a non-zero threshold value deemed to represent an operational baseline. In sum, controller 28 determines what adjustment should be made to the operating speed of vapor pump 26 to effect the required change in induced flow rate. A signal generator is provided by controller 28 to convert the pump speed adjustment data into pump control signal 36 representative of the required flow rate and suitable for varying the operating speed of vapor pump 26. Vapor pump 26 is responsive to the pump control signal 36 provided by controller 28 and adjusts its operating speed, and hence the induced vapor flow rate, in accordance with the pump control signal 36. The vapor pump flow rate will, in general, be subject to reduction or termination with declining levels of detected hydrocarbon. Controller 28 may be any suitable device or component for implementing the indicated control functions. For example, controller 28 may be an analog control circuit or a programmable digital microprocessor known to those skilled in the art. The necessary interconnections and interfacing between and among the subsystems of vapor recovery system 18 are conventional arrangements known to those skilled in the art. The vapor recovery system 18 preferably operates on a continuous basis for the duration of any refueling activity. This operational mode will feature a continuous supply of frequency shift measurements provided to controller 28 from the coated crystal oscillator, and automatic adjustment of the operating speed of vapor pump 26 based on the hydrocarbon concentration represented by the frequency shifts. The flow rate generated by vapor pump 26 is thereby continuously regulated to minimize the presence of atmospheric air in the collected vapors.

Referring to FIG. 2, there is shown a block diagram illustration of a circuit configuration for the crystal oscillator sensor module 30 in FIG. 1, according to a preferred embodiment of the present invention. The illustrated circuit configuration includes a coated crystal oscillator 40 of the type discussed in connection with FIG. 1. In particular, oscillator 40 generates a detection frequency signal having a frequency of oscillation that is shifted relative to its fundamental resonance frequency in response to and in accordance with the extent of interaction between the coating layer of the crystal oscillator and any hydrocarbon in the vapor emissions. There is further provided a reference oscillator 42 for generating a reference frequency signal having a frequency of oscillation corresponding to the fundamental resonant frequency of oscillator 40. Mixer 44 performs a frequency multiplication operation involving the detection frequency signal and the reference frequency signal to produce a beat frequency signal representing the frequency shift due to the hydrocarbon interaction. Converter 46 is responsive to the beat frequency signal and converts the frequency shift thereby represented into an electrical signal suitable for application to components governed by electrical activation (e.g., vapor pump 26).

The present invention is concerned with the detection of hydrocarbons in the vapor path of gasoline dispensers. Normally such sensing is difficult due to the high hydrocarbon concentration and a potentially condensing atmosphere. Furthermore, most hydrocarbon sensors do not perform well in vapors and liquids. The invention described herein discloses a coated oscillator having a property of not being affected by high liquid or gas concentrations. The sensor has the potential to be heated, causing rapid evaporation of condensate, making it a candidate for this type of gasoline dispenser application.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A system for recovering vapor emissions from a fuel receiving tank, comprising:

vapor collection means, disposed in vapor communicating relationship with respect to said fuel receiving tank, for controllably collecting vapor emissions from said fuel receiving tank;

crystal oscillator means, exposed for contact with vapor emissions emanating from said fuel receiving tank and adapted to exhibit a shift from its fundamental resonance frequency in response to the presence of hydrocarbon, for generating a frequency shift signal having a frequency of oscillation representative of a hydrocarbon concentration within vapor emissions exposed to said crystal oscillator means; and controller means, operatively coupled to said vapor collection means and to said oscillator means, for controllably adjusting the rate of vapor collection by said vapor collection means in accordance with said frequency shift signal.

2. The system as recited in claim 1, wherein said crystal oscillator means further comprises:

a contact structure capable of interacting with hydrocarbon upon exposure thereto and effective in inducing said shift in resonance frequency in response to the presence of hydrocarbon interacting therewith.

3. The system as recited in claim 1, wherein said crystal oscillator means further comprises:

a resonant crystal structure including at least one surface thereof coated with a material having an affinity for hydrocarbon accretion.

4. The system as recited in claim 3, wherein the affinity of said coating material for hydrocarbon accretion is defined by an activity of reversible absorption.

5. The system as recited in claim 3, wherein the affinity of said coating material for hydrocarbon accretion is defined by an activity of reversible adsorption.

6. The system as recited in claim 1, further comprises:

reference crystal oscillator means for generating a reference frequency signal at said fundamental resonance frequency;

mixing means, responsive to the frequency shift signal from said crystal oscillator means and the reference frequency signal from said reference crystal oscillator means, for generating a beat signal indicative of the frequency differential therebetween; and conversion means, operatively coupled to said mixing means, for providing a control signal in accordance with said frequency differential.

7. The system as recited in claim 1, wherein said vapor collection means comprises:

vapor pump means for controllably generating a variable vacuum action that is effective in drawing vapor emissions away from said fuel receiving tank.

8. The system as recited in claim 7, wherein said controller means further includes:

vapor flow rate control means, coupled to said vapor pump means and said vapor collection means, for varying the vacuum action of said vapor pump means as a function of the frequency shift signal generated by said crystal oscillator means.

9. A system for fueling a receiving tank, comprising:

fuel dispensing means for dispensing fuel into an inlet of said receiving tank;

vapor capturing means, disposed in vapor communicating relationship with respect to the inlet of said receiving tank, for controllably acquiring vapor emissions emanating from said receiving tank;

sensor means disposed in vapor sensing relationship with respect to the inlet of said receiving tank for sensing vapor emissions emanating therefrom, said sensor means being adapted for operation in the absence of vapor emissions for generating an oscillatory signal at a fundamental frequency, and being adapted for operation in the presence of vapor emissions for generating an oscillatory signal at a frequency that is shifted relative to is said fundamental frequency in accordance with a hydrocarbon concentration within said sensed vapor emissions; and controller means, operatively coupled to said vapor capturing means and to said sensor means, for controlling the acquisition of vapor emissions by said vapor capturing means as a function of said frequency shift.

10. The system as recited in claim 9, wherein said sensor means further comprises:

crystal oscillation circuit means, adapted for interaction with hydrocarbon, for generating a resonant frequency output signal having an oscillation frequency influenced by and indicative of the concentration of hydrocarbon in the vapor emissions sensed by said sensor means.

11. The system as recited in claim 10, wherein the oscillation frequency of said generated output signal exhibits a frequency shift relative to a fundamental resonant frequency.

12. The system as recited in claim 11, wherein said oscillation circuit means further includes:

a contact structure exhibiting a sensitivity to hydrocarbon defined by an interaction therewith that induces said frequency shift.

13. The system as recited in claim 11, wherein said oscillation circuit means further includes:

a resonant crystal structure having a coating layer formed thereon and capable of interacting with hydrocarbon.

14. A system for detecting vapor emissions including hydrocarbon emanating from a fuel receiving tank, comprising:

vapor collection means for controllably collecting vapor emissions emanating from said fuel receiving tank;

vapor monitoring means, disposed for exposure to said vapor emissions and including an oscillation means comprising a resonant structure having a contact layer formed thereon and capable of interacting with hydrocarbon, for sensing said vapor emissions and for providing an oscillatory signal generated by said resonant structure and characterized by a frequency of oscillation defining a shift from a fundamental resonance frequency and indicating the hydrocarbon concentration in said sensed vapor emissions; and controller means, operatively coupled to said vapor collection means and responsive to the oscillatory signal provided by said vapor monitoring means, for variably controlling the collection of vapor emissions by said vapor collection means in accordance with the frequency shift defined by the oscillation frequency of said oscillatory signal.

15. The system as recited in claim 14, wherein the contact layer of said resonant structure includes a deposition coating capable of supporting hydrocarbon accretion through absorptive activity.

16. The system as recited in claim 14, wherein the contact layer of said resonant structure includes a deposition coating capable of supporting hydrocarbon accretion through adsorptive activity.

17. A method of recovering vapors from a fuel storage tank, comprising the steps of:

collecting said vapors with a controllable pumping action generating an adjustable vapor flow rate;

providing a resonant crystal structure having a contact structure capable of interacting with hydrocarbon upon exposure thereto and operative to generate a resonance signal having a frequency of oscillation determined by the level of hydrocarbon interaction in said contact structure;

exposing said resonant structure for contact with vapor emissions emanating from said fuel storage tank; and controlling said pumping action to adjust said vapor flow rate in accordance with the frequency of oscillation of said resonance signal.

18. The method as recited in claim 17, wherein the step of controlling said pumping action further includes the steps of:

determining a frequency differential between the oscillation frequency of said resonance signal and a fundamental resonance frequency of said resonant crystal structure;

converting the determined frequency differential to a control signal representative of hydrocarbon concentration in said vapor emissions; and adjusting said vapor flow rate in accordance with said control signal.

* * * * *